United States Patent
Stutman et al.

(10) Patent No.: US 9,439,613 B2
(45) Date of Patent: *Sep. 13, 2016

(54) SYSTEM AND METHOD FOR PHASE-CONTRAST X-RAY IMAGING

(71) Applicant: THE JOHNS HOPKINS UNIVERSITY, Baltimore, MD (US)

(72) Inventors: Dan Stutman, Cockeysville, MD (US); Michael Finkenthal, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 213 days.

This patent is subject to a terminal disclaimer.

(21) Appl. No.: 14/174,830

(22) Filed: Feb. 6, 2014

(65) Prior Publication Data

US 2014/0226785 A1    Aug. 14, 2014

Related U.S. Application Data

(60) Provisional application No. 61/763,683, filed on Feb. 12, 2013.

(51) Int. Cl.
*G01N 23/207* (2006.01)
*G06K 9/20* (2006.01)
(Continued)

(52) U.S. Cl.
CPC ........... *A61B 6/484* (2013.01); *A61B 6/4035* (2013.01); *G01N 23/20008* (2013.01); *G01N 23/20075* (2013.01); *G02B 5/1814* (2013.01); *G02B 5/1819* (2013.01); *G02B 5/1871* (2013.01); *G01N 23/046* (2013.01); *G01N 23/207* (2013.01); *G01N 2015/1454* (2013.01); *G01N 2021/4186* (2013.01); *G01N 2223/419* (2013.01); *G02B 5/1838* (2013.01); *G02B 5/1842* (2013.01); *G02B 6/02085* (2013.01);
(Continued)

(58) Field of Classification Search
CPC ...... A61B 6/48; A61B 6/484; A61B 6/4035; A61B 2018/2294; G02B 6/02057; G02B 6/02076; G02B 6/0208; G02B 6/02085; G02B 6/02209; G02B 5/18; G02B 5/1809; G02B 5/1814; G02B 5/1819; G02B 5/1828; G02B 5/1838; G02B 5/1842; G02B 5/1866; G02B 5/1871; G02B 5/1876; G02B 5/188; G02B 5/1885; G02B 5/32; G21K 2207/00; G21K 2207/005; G06K 9/20; G06K 9/2036; G01N 2015/1454; G01N 2021/4173; G01N 2021/4186; G01N 23/20; G01N 23/20008; G01N 23/20075

See application file for complete search history.

(56) References Cited

U.S. PATENT DOCUMENTS 8,767,915 B2 *  7/2014 Stutman ............... G01N 23/04
                                                   378/156
2007/0183579 A1  8/2007 Baumann et al.
(Continued)

OTHER PUBLICATIONS

International Search Report dated Apr. 30, 2015 from International Application No. PCT/US2015/011082, pp. 1-15.
Cai, Weixing et al. Dose efficiency consideration for volume-of-interest breast imaging using x-ray differential phase-contrast CT. Proc. of SPIE, 2009, vol. 7258, pp. 1-9.
Lauzier, Pascal T. et al. Interior tomography in x-ray differential phase contrast CT imaging. Phys. Med. Biol., 2012, vol. 57, pp. N117-N130.
(Continued)

*Primary Examiner* — Anastasia Midkiff
(74) *Attorney, Agent, or Firm* — MH2 Technology Law Group LLP

(57) ABSTRACT

A differential phase contrast X-ray imaging system includes an X-ray illumination system, a beam splitter arranged in a radiation path of the X-ray illumination system, and a detection system arranged in a radiation path to detect X-rays after passing through the beam splitter.

16 Claims, 11 Drawing Sheets

(51) Int. Cl.
　　　*G02B 5/18*　　　(2006.01)
　　　*A61B 6/00*　　　(2006.01)
　　　*G01N 23/20*　　(2006.01)
　　　*G01N 23/04*　　(2006.01)
　　　*G02B 6/02*　　　(2006.01)
　　　*G01N 15/14*　　(2006.01)
　　　*G01N 21/41*　　(2006.01)

(52) U.S. Cl.
　　　CPC ....... *G06K 9/2036* (2013.01); *G21K 2207/005* (2013.01)

(56) References Cited

U.S. PATENT DOCUMENTS

| | | | |
|---|---|---|---|
| 2008/0251738 A1* | 10/2008 | Figueroa | G02B 27/646 250/504 R |
| 2009/0092227 A1 | 4/2009 | David et al. | |
| 2010/0220832 A1* | 9/2010 | Ning | A61B 6/032 378/4 |
| 2012/0099702 A1 | 4/2012 | Engel et al. | |
| 2012/0099705 A1 | 4/2012 | Murakoshi et al. | |
| 2013/0028378 A1* | 1/2013 | Stutman | G01N 23/04 378/62 |

OTHER PUBLICATIONS

Li, Ke et al. Differential phase contrast tomosynthesis imaging. Proc. of SPIE, 2012, vol. 8313, pp. 1-6.

Li, Jiangkun et al. Phantom Study for Volume-of-Interest Breast Imaging using Differential Phase Contrast Cone Beam CT (DPC-CBCT). Proc. of SPIE, 2013, vol. 8668, pp. 1-8.

Shimao, Daisuke et al. Shift-and-add tomosynthesis of a finger joint by X-ray dark-field imaging: Difference due to tomographic angle. European Journal of Radiology, 2006, vol. 68S, pp. S27-S31.

Stutman, D. et al. Glancing angle Talbot-Lau grating interferometers for phase contrast imaging at high x-ray energy. Applied Physics Letters, 2012, vol. 101, pp. 091108-1-091108-5.

Stutman, D. et al. High Energy X-ray Phase-Contrast Imaging Using Glancing Angle Grating Interferometers. Proc. of SPIE, 2013, vol. 8668, pp. 1-8.

Sunaguchi, N. et al. Refractive-index based tomosynthesis using dark-field imaging optics. Journal of Physics: Conference Series, 2013, vol. 425, pp. 1-5.

Zanette, I. et al. Interlaced phase stepping in phase-contrast x-ray tomography. Applied Physics Letters, 2011, vol. 98, pp. 094101-1-094101-3.

* cited by examiner

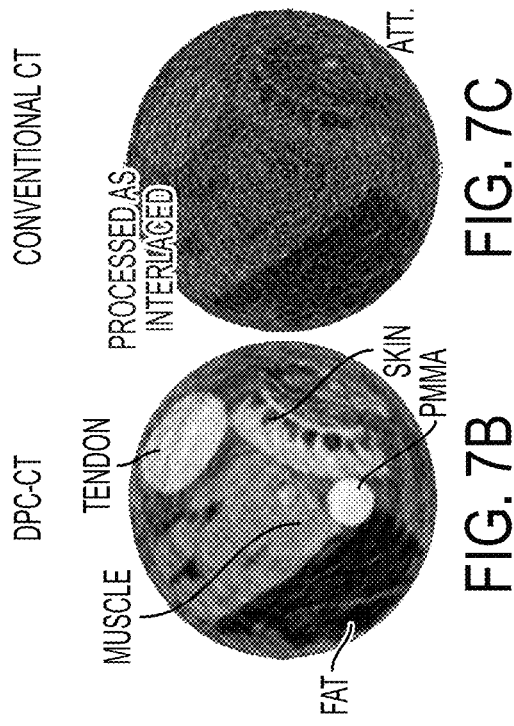
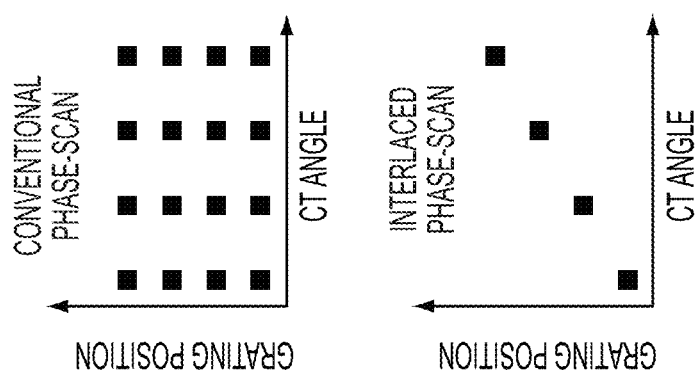
FIG. 7A
FIG. 7B
FIG. 7C

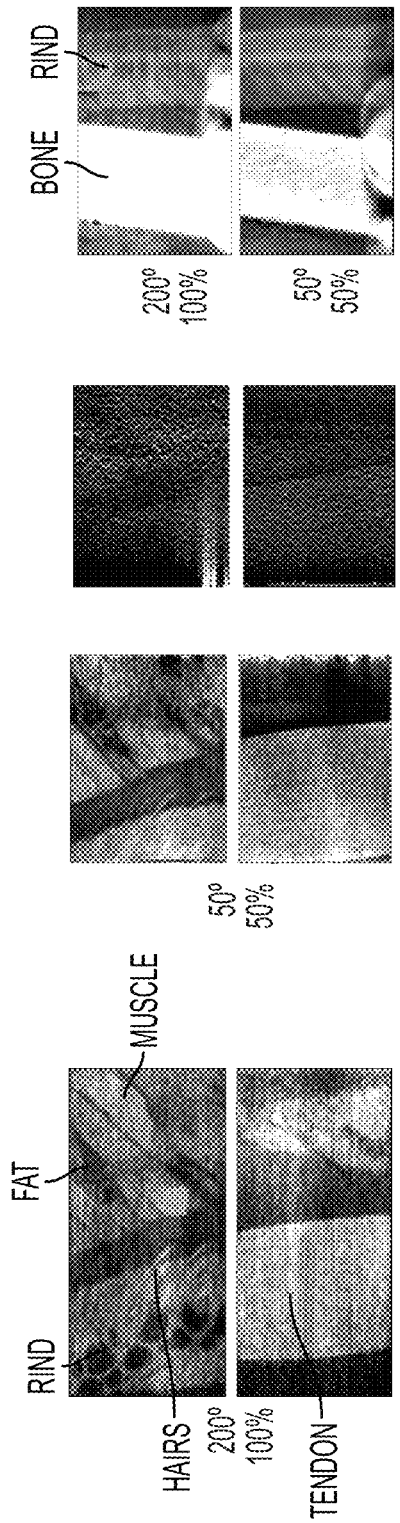

SYSTEM AND METHOD FOR PHASE-CONTRAST X-RAY IMAGING

CROSS REFERENCE TO RELATED APPLICATIONS

This application is related to U.S. patent application Ser. No. 13/493,392, titled "Differential Phase Contrast X-ray Imaging System and Components," filed on Jan. 31, 2013, U.S. patent application Ser. No. 14/176,655, titled "Large Field of View Grating Interferometers for X-ray Phase Contrast Imaging and CT at High Energy," filed Aug. 14, 2014 by Dan Stutman and Michael Finkenthal, and claims priority from U.S. Provisional Patent Application 61/763, 683 titled "High Energy X-Ray Phase Contrast CT Systems Using Tiled Glancing Incidence Gratings," filed on Feb. 12, 2013, hereby incorporated by reference in their entirety.

GOVERNMENT RIGHTS

This invention was made with government support under Grant No. 1R21EB012777-01A awarded by the Department of Health and Human Services, The National Institutes of Health (NIH). The government has certain rights in the invention.

FIELD

This disclosure relates to X-ray systems, and more particularly to differential phase contrast X-ray imaging systems and X-ray illumination systems.

BACKGROUND

X-ray differential phase-contrast (DPC) imaging relies on the refraction of the X-rays passing through an object. Since for hard X-rays the refraction angles are in the μ-radian range, the basic technique used for DPC imaging is to angularly filter with μ-radian resolution the transmitted X-ray beam, thus converting the angular beam deviations from refraction into intensity changes on a conventional detector. The angular filtering is done using X-ray optics such as crystals or gratings.

A fundamental advantage of DPC imaging is that it is sensitive to density gradients in the measured object rather than to its bulk X-ray absorption. In medical imaging for instance, refraction has a contrast enhancing effect at tissue boundaries, which enables the detection of soft tissues which are otherwise invisible in conventional X-ray imaging. The ultra-small angle scattering occurring in micro-structured soft tissue such as cartilage, tendon, ligament or muscle has also a volume contrast enhancing effect. Another benefit of DPC for medical imaging is that it can improve contrast and resolution at similar or lower dose than in conventional X-ray imaging. This is possible because DPC uses X-rays that are not absorbed by the body and because the soft tissue refraction coefficients decrease with X-ray energy much slower than the absorption ones. In particular, by using for DPC a spectrum with mean energy in the 50-80 keV range approximately, the soft tissue dose is minimized while refraction strongly dominates over absorption.

X-ray phase-contrast is also of interest for imaging and non-destructive characterization in material sciences, in particular as concerns low-Z materials. The structure and defects of materials ranging from polymers, to fiber composites, to wood, and to engineered bio-materials can be probed on the micrometer scale using X-ray phase-contrast. Some of the techniques used for X-ray phase-contrast can also be applied with neutrons. Recently X-ray phase-contrast has gained attention in fusion energy research, where the capability of refraction based imaging to measure the density gradients in an object can be used for the diagnostic of high density plasmas in inertial confinement fusion (ICF) and other high energy density physics (HEDP) experiments.

Until recently, research on X-ray DPC imaging has been done mostly at synchrotrons, using crystal optics; the high intensity of the synchrotron compensates for the low efficiency (less than a hundredth of a %) of the crystal optics. Although there are efforts to develop table-top synchrotrons, or to use narrow $K_\alpha$ lines from conventional tubes, the crystal method has not yet entered the domain of practical applications. It is thus of interest to develop more efficient DPC methods and optics, that can work with conventional medical or industrial X-ray tubes.

A DPC method that can work with conventional X-ray sources is the Talbot-Lau shearing interferometry, in which micro-periodic optics such as gratings are used to angularly filter the refracted X-rays with μ-radian resolution. The Talbot interferometer includes first a 'beam-splitter' (typically a π-shift phase grating), which divides (or 'shears') through the Talbot effect the incoming beam into few μ-radian wide beamlets. The Talbot effect consists in a 'replication' of the grating pattern by the wave intensity, at periodic distances along the beam, called Talbot distances, $d_T = k/\eta^2 \cdot g^2/(2\lambda)$, with λ the X-ray wavelength, g the grating period, k=1, 2, . . . the order of the pattern, and η=1 for a π/2 phase shifting grating or for an absorption grating, and η=2 for a π phase grating. The beamsplitter thus creates at the 'Talbot distance' a micro-periodic fringe pattern, which changes shape (shifts) with respect to the unperturbed pattern when a refractive object is introduced in the beam. The differential phase-contrast imaging consists thus in measuring the changes in the fringe pattern induced by the object, with respect to the pattern without the object. To achieve μ-radian angular sensitivity at hard X-ray wavelengths, the period g must be in the μm range, resulting in a Talbot distance of a few tens of cm.

The fringe pattern can in principle be directly measured using a microscopic pixel detector. This is however quite inefficient. For most practical applications, the fringe pattern changes are converted into intensity changes on a macroscopic pixel detector by introducing an 'analyzer' absorption grating placed behind the beam-splitter and having the period of the Talbot pattern. Lastly, for such an interferometer to function with an extended spot X-ray tube, a 'source' absorption grating is placed in front of the source, thus dividing it into an array of quasi-coherent line sources.

The gratings are made by micro-lithography in thin Si wafers or photoresist. The absorption gratings are difficult to fabricate; they are typically made by filling with gold the gaps in regular transmission gratings. The 'grating shearing method' described above has demonstrated performance similar to the crystal method at energies below a few tens of keV.

This method is however less useful at energies above a few tens of keV. The reason is that it is difficult to fabricate micron-period absorption gratings with the thickness required to block higher energy X-rays. This is illustrated in FIG. 1A with a plot of the Au thickness needed for 95% absorption, as a function of the photon energy. As seen, several hundred μm depth gratings would be needed in the range of interest for clinical DPC imaging. Depending on the grating period, the present technological limit is however around 50-100 μm. This limits the contrast of the grating shearing method for high energy X-rays, as illustrated in FIG. 1B by the fringe contrast computed for an interferometer having 100 µm thick, 4 µm period Au analyzer grating (throughout this specification we used for X-ray phase-contrast and optics calculations the XWFP wave propagation code and the XOP optics package).

Accordingly, it is desirable to develop improved types of optics to enable efficient DPC imaging at X-ray energies above a few tens of keV.

SUMMARY

In accordance with implementations of the present disclosure, a differential phase contrast X-ray imaging system is disclosed. The imaging system can include an X-ray illumination system; a beam splitter grating arranged in a radiation path of the X-ray illumination system and operable to receive an incident X-ray beam and provide an interference pattern of X-rays; and a detector system arranged in a radiation path to detect X-rays after passing through the beam splitter grating and in a Talbot-Lau interferometer configuration with the beam splitter grating. The detector system can include a X-ray detector and an analyzer grating, wherein the analyzer grating is operable to intercept and block at least a portion of the interference pattern of X-rays before reaching the X-ray detector, wherein the beam splitter grating and the analyzer grating are arranged at a shallow angle relative to incident X-rays.

In implementations, the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the longitudinal dimension and being spaced substantially parallel to each other in the lateral dimension such that there are optically rare regions between adjacent optically dense regions, wherein each optically dense region has a depth in the transverse dimension that is smaller than a length in the longitudinal dimension, wherein the analyzer grating is arranged with the longitudinal dimension at the shallow angle, wherein the shallow angle is less than 30 degrees.

In implementations, the beam splitter grating is a transmission grating.

In implementations, the analyzer gratings include more than one grating tiled on top of another grating.

In implementations, the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the lateral dimension and being spaced in a divergent geometry from each other such that there are optically rare regions between adjacent optically dense regions, wherein each optically dense region has a depth in the transverse dimension that is smaller than a length in the longitudinal dimension and the lateral dimension, wherein the analyzer grating is arranged with the lateral dimension at the shallow angle, wherein the shallow angle is less than 30 degrees.

In implementations, the X-ray illumination system can include an X-ray source; and a source grating arranged in a radiation path between the X-ray source and the beam splitter grating, wherein the source grating provides a plurality of substantially coherent X-ray beams.

In implementations, the imaging system can include a vibration resistant mount operable to provide a support to the source grating, the beam-splitter grating, the analyzer grating.

In implementations, the imaging system can include a rotation stage operable to rotate the X-ray illumination system, the beam splitter grating, the detection system about an object.

In implementations, the beam splitter grating and the analyzer grating have grating patterns determined according Talbot-Lau conditions.

In implementations, a field of view of the detector system is sized to image a human extremity.

In implementations, the detection system is operable to capture a single image for each angle at which the rotation stage is rotated.

In accordance with implementations of the present disclosure, a differential phase contrast X-ray imaging method is disclosed. The method can include providing an incident X-ray beam using an X-ray illumination system; receiving the incident X-Ray beam at a beam splitter grating that is arranged in a radiation path of the X-ray illumination system and providing an interference pattern of X-rays; and detecting, using a detecting system arranged in a radiation path, X-rays after passing through the beam splitter grating that is in a Talbot-Lau interferometer configuration with the beam splitter grating, wherein the detector system comprises a X-ray detector and an analyzer grating, wherein the analyzer grating is operable to intercept and block at least a portion of the interference pattern of X-rays before reaching the X-ray detector, wherein the beam splitter grating and the analyzer grating are arranged at a shallow angle relative to incident X-rays.

In implementations, the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the longitudinal dimension and being spaced substantially parallel to each other in the lateral dimension such that there are optically rare regions between adjacent optically dense regions, wherein each optically dense region has a depth in the transverse dimension that is smaller than a length in the longitudinal dimension, wherein the analyzer grating is arranged with the longitudinal dimension at the shallow angle, wherein the shallow angle is less than 30 degrees.

In implementations, the analyzer grating comprises more than one grating tiled and stacked on top of another grating.

In implementations, the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the lateral dimension and being spaced in a divergent geometry from each other such that there are optically rare regions between adjacent optically dense regions, wherein each optically dense region has a depth in the transverse dimension that is smaller than a length in the longitudinal dimension and the lateral dimension, wherein the analyzer grating is arranged with the lateral dimension at the shallow angle, wherein the shallow angle is less than 30 degrees.

In implementations, the method can include receiving the incident X-ray beam at a source grating that arranged in a radiation path between a X-ray source and the beam splitter grating; and proving a plurality of substantially coherent X-ray beams to the beam splitter grating.

In implementations, the method can include rotating a rotation stage that is operable to support the X-ray illumination system, the beam splitter grating, the detection system about an object.

In implementations, the method can include determining grating patterns for the beam splitter grating and the analyzer grating according to Talbot-Lau conditions.

In implementations, a field of view of the detector system is sized to image a human extremity.

In implementations, the method can include capturing a single image for each angle at which the rotation stage is rotated.

It is to be understood that both the foregoing general description and the following detailed description are exemplary and explanatory only and are not restrictive of the invention, as claimed.

Additional features, implementations, and embodiments consistent with the disclosure will be set forth in part in the description which follows, or may be learned by practice of the disclosure. The metes and bounds of the invention will be defined by means of the elements and combinations particularly pointed out in the appended claims.

BRIEF DESCRIPTION OF THE DRAWINGS

The accompanying drawings, which are incorporated in and constitute a part of this specification, illustrate embodiments of the disclosure and together with the description, serve to explain the principles of the disclosure. In the figures:

FIG. 4A shows a large FOV analyzer grating using three tiled wafers, FIG. 4B shows a side view of the scanner, and FIG. 4C shows a top view of the scanner.

FIG. 7A shows an interlaced phase-scan method consistent with embodiments of the disclosure; FIGS. 7B and 7C shows DPC-CT and attenuation-CT images of fresh pig soft tissue phantom obtained at 65 kVp/45 keV mean energy with clinically compatible does, respectively.

FIG. 9A shows a full-coverage/full scan images of tissue phantom, FIGS. 9B and 9C show DPC and attenuation images, respectively, with limited-coverage/limited-angle scan, and FIG. 9D shows a full-coverage/full-scan and limited-coverage/limited-scan DPC images of bone/soft tissue phantom.

DETAILED DESCRIPTION OF THE EMBODIMENTS

Reference will now be made in detail to exemplary embodiments of the invention, examples of which are illustrated in the accompanying drawings. Wherever convenient, the same reference numbers will be used throughout the drawings to refer to the same or like parts.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

Figure 2:
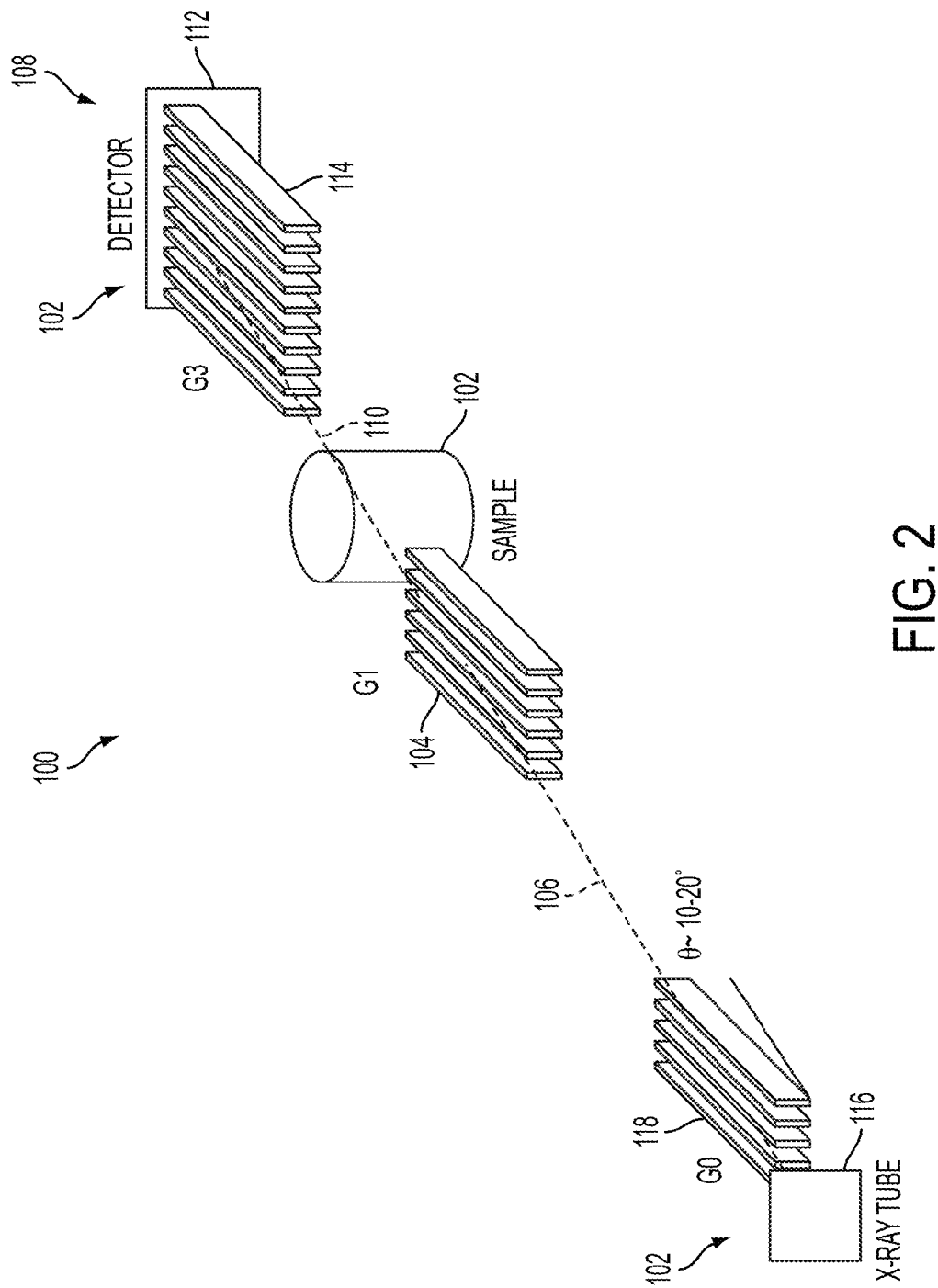
FIG. 2 shows an optical layout of a glancing angle interferometer consistent with embodiments of the disclosure.

Implementations of the present disclosure relate to applying the GAI in conjunction with single-image phase retrieval methods and with ROI/limited-angle CT reconstruction methods, for high energy (80-140 kVp) phase-contrast imaging of the internal organs and tissues with clinically compatible dose. For brevity, this multi-solution approach is termed GAI tomosynthesis, or GAI-TS. There are numerous reasons why GAI-TS is successful for internal organs and tissues. First, the GAI enables achieving high interferometer contrast throughout the 80-140 kVp energy range, because the Au absorption strongly increases above the K-edge at 80 keV. A FOV of the order of a few by a few inch at the object, which is achieved with tiled and stacked GAI gratings as in FIG. 2, is adequate for ROI imaging of the internal organs. The internal organs can be viewed over a limited angular range without traversing the thick bone in the spine, which allows maintaining high interferometer contrast through the thick soft tissues in the torso. The limited coverage/limited-angle in the present GAI-TS can reduce both the exposure and scan time compared to full coverage/full-scan DPC-CT. Reducing the overall exposure by restricting the FOV and scanned area is useful because high spatial resolution is desired in DPC, which in turn requires more photons per unit area. Restricting the scan angle will also make the scan time more clinically attractive, because DPC typically requires a longer exposure per CT view than conventional imaging, due to photon loss in the gratings.

FIG. 2 shows an example schematic illustration of a differential phase contrast X-ray imaging system 100 according to an embodiment of the present disclosure. The differential phase contrast X-ray imaging system 100 includes an X-ray illumination system 102, a beam splitter 104 arranged in an optical path 106 of the X-ray illumination system 102, and a detection system 108 arranged in an optical path 110 to detect X-rays after passing through the beam splitter 104. The detection system 108 includes an X-ray detection component 112. The beam splitter 104 includes a splitter grating arranged to intercept an incident X-ray beam and provide an interference pattern of X-rays. By way of a non-limiting example, beam splitter 104 can be a thin phase grating made of Si or Ni.

The detection system 108 also includes an analyzer grating 114 arranged to intercept and block at least portions of the interference pattern of X-rays prior to reaching the X-ray detection component 112. The analyzer grating 114 has a longitudinal dimension, a lateral dimension that is orthogonal to the longitudinal dimension, and a transverse dimension that is orthogonal to the longitudinal and lateral dimensions. The analyzer grating 114 has a pattern of optically dense regions, each having a longest dimension along the longitudinal dimension and spaced substantially parallel to each other in the lateral dimension such that there are optically rare regions between adjacent optically dense regions.

Each optically dense region has a depth in the transverse dimension that is smaller than a length in the longitudinal dimension. The analyzer grating 114 is arranged with the longitudinal dimension at a shallow angle α relative to incident X-rays such that the shallow angle α is less than 30 degrees. The longitudinal dimension of the analyzer grating 114 is oriented substantially along the optical path 110 (which can be the optical axis, for example), except tilted at the shallow angle α. (This will also be referred to as a glancing angle.)

In an embodiment of the current disclosure, each optically dense region has a depth in the transverse dimension that is smaller than a length in the longitudinal dimension by at least a factor of two. In an embodiment, each optically dense region has a depth in the transverse dimension that is smaller than a length in the longitudinal dimension by at least a factor of ten. In a further embodiment, each optically dense region has a depth in the transverse dimension that is smaller than a length in the longitudinal dimension by at least a factor of one hundred.

In an embodiment of the current disclosure, the shallow angle α is less than 25 degrees and greater than 5 degrees. In another embodiment, the shallow angle α is less than 15 degrees and greater than 3 degrees. An embodiment of the current disclosure is directed to medical applications. Since it is difficult to produce few-micron period gratings with more than ~100 μm Au absorber thickness, inclining the gratings at an angle in the 5-25° range makes for 200-1000 μm effective Au thickness. As is shown in FIG. 1, this thickness enables >90% X-ray absorption (and thus high interferometer contrast) over the ~40 keV-110 keV energy range, of interest for medical phase-contrast imaging deep in the body. Another embodiment is directed to industrial or non-destructive testing (NDT) applications. Using glancing angles in the 3-15° range, the effective Au thickness is in the 400-2000 μm range, which makes for good X-ray absorption and interferometer contrast in the ~100 keV-250 keV energy range of interest for industrial NDT applications.

In an embodiment of the current disclosure, the splitter grating 104 is a reflection grating (not shown). In an embodiment of the current invention, the splitter grating 104 is a transmission grating. According to an embodiment of the current disclosure in which the splitter grating 104 is a transmission grating, similar to analyzer grating 114, such an embodiment of the analyzer grating has a longitudinal dimension, a lateral dimension that is orthogonal to the longitudinal dimension, and a transverse dimension that is orthogonal to the longitudinal and lateral dimensions. The splitter grating 104 in this embodiment has a pattern of optically dense regions, each having a longest dimension along the longitudinal dimension and being spaced substantially parallel to each other in the lateral dimension such that there are optically rare regions between adjacent optically dense regions. Each optically dense region has a depth in the transverse dimension that is smaller than a length in the longitudinal dimension. The splitter grating 104 is arranged with the longitudinal dimension at a shallow angle α relative to incident X-rays such that it is less than 30 degrees. In some embodiments, the splitter grating 104 can be similar in construction as the analyzer grating 114 and arranged similarly at a shallow angle α as described above with respect to the analyzer grating 114, although placed at a different position along the optical axis.

As used herein, the term "block" X-rays is intended to mean that sufficient attenuation is achieved relative to X-rays that pass through the optically rare regions of the grating to permit a useful contrast for the particular application. It is not intended to require absolutely 100% attenuation.

The splitter grating 104 and the analyzer grating 114 are arranged with a separation determined according to Talbot-Lau conditions according to some embodiments of the present disclosure. In some embodiments, the splitter grating 104 and the analyzer grating 114 have grating patterns that are determined according to Talbot-Lau conditions.

The X-ray illumination system 102, according to some embodiments of the present disclosure can include an X-ray source 116, and a source grating 118 arranged in an optical path between the X-ray source 116 and the beam splitter 104. The source grating 118 provides a plurality of substantially coherent X-ray beams when X-ray source 116 is a spatially extended source of X-rays, as is illustrated schematically in FIG. 2. However, the broad concepts of the present disclosure are not limited to the particular embodiment illustrated in FIG. 2. The X-ray illumination system 102 can include combinations of one or more gratings and mirrors, including both transmission and/or reflection gratings. By way of a non-limiting example, the source grating 118 and the analyzer grating 114 are absorption gratings made of Au.

Figure 3A:
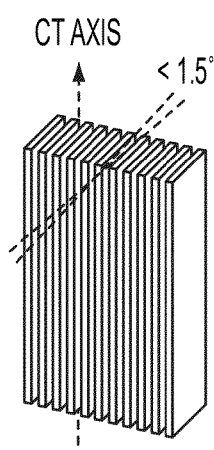
FIG. 3A shows the horizontal FOV (field of view) vignetting in conventional interferometer.
Figure 3B:
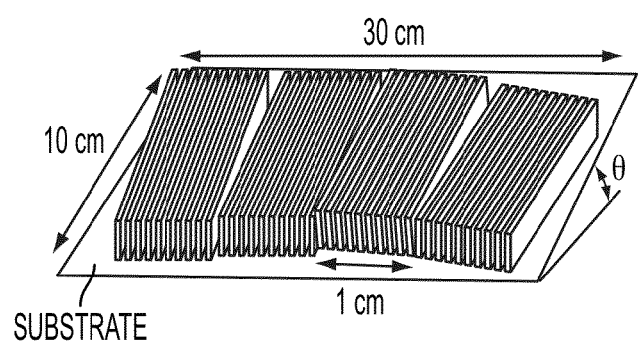
FIG. 3B shows a 'tiled' GAI grating layout for wide FOV at high energy consistent with embodiments of the disclosure.
Figure 3C:
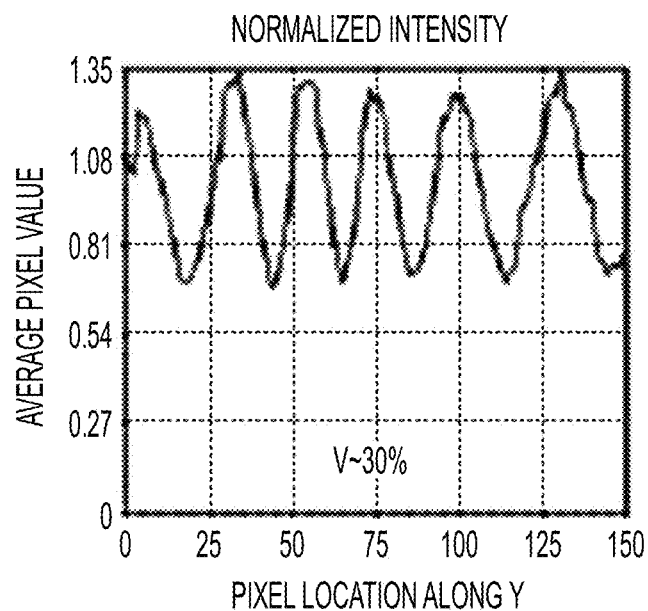
FIG. 3C shows the experimental GAI interferometer contrast at 80 kVp through 200 mm water.
Figure 3D:
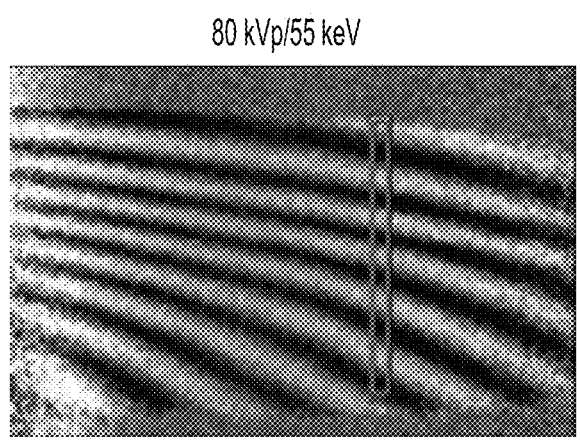
FIG. 3D shows the experimental GAI interferometer contrast with grating rotated and moved 10 cm off the beam axis, validating the 'tiled' grating design in FIG. 3B.

FIG. 3A shows an example vertical arrangement of a grating used in a convention Talbot-Lau interferometer with the gratings arranged lengthwise with the CT axis providing a limited lateral FOV due to the horizontal vignetting or collimation by the narrow and deep grating openings, that have angular width typically less than 1.5°. FIG. 3B shows an example glancing angle design that overcomes the problems of the convention arrangement in accordance with implementation of the present disclosure. The glancing angle design comprises a fan-shaped array of 'sub-gratings' with slightly rotated lines made on a single substrate or wafer. All the sub-gratings can have equal period and width, where the width of the sub-gratings is comparable (equal or less than) to the full width at half max (FWHM) of the vignetting curve (e.g., 10 mm for a 10 µm period grating at 10° angle) and the grating pattern is rotated to match the X-ray fan beam direction. The rotation angle can follow the central ray direction for each sub-grating, such that the incident X-rays 'see' an array of collimators that are with good approximation aligned to the ray direction, thus minimizing the vignetting. For example, a 6" Si wafer would accommodate 12 sub-gratings of 10 mm width and 90 mm height, giving a FOV at the detector of 120 mm width and 30 mm height, at a glancing angle of 20°. Several such wafers side by side would cover a contiguous FOV of a few tens of cm wide, which is sufficient for full cone-beam CT or large objects. The sub-gratings can be arranged to have a fan angle between about 5°-15°. In some implementations, the GAI gratings can comprise multiple 'tilted' micro-periodic gratings having the absorption bars tilted at a glancing angle along the direction of the incident radiation, and also aligned parallel with the incident X-rays. The tiled GAI gratings can have slightly variable period along the grating bar direction. One benefit of this approach is that the sub-gratings are pre-aligned with nanometer precision through the lithography manufacturing process. The design was experimentally tested by translating 100 mm off-axis and simultaneously rotating by a few degrees the gratings in the 10 µm period GAI. FIG. 3C shows that high contrast fringes are obtained in the setup, which confirms the feasibility of the tiled glancing angle grating solution. The decreased vertical FOV of the single grating GAI can be compensated by vertically stacking multiple gratings as in 4B. By way of one non-limiting example, the GAI gratings can be tiled and stacked to provide a FOV up to about 10×30 cm.

Figure 5:
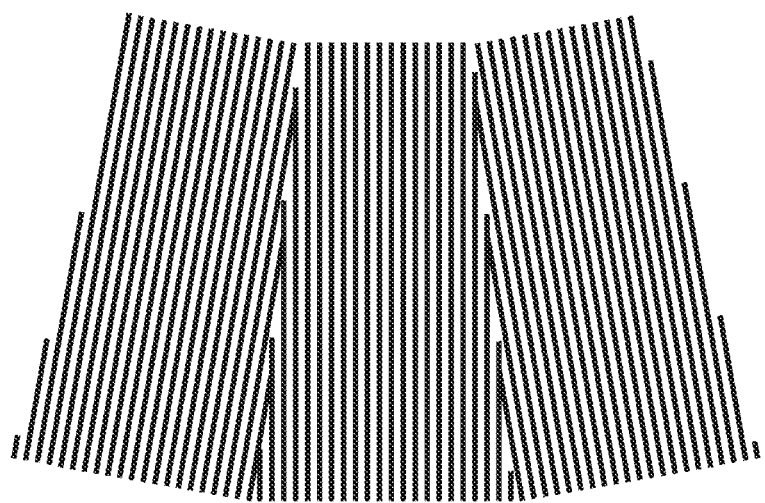
FIG. 5 shows a method for joining tiled GAI gratings consistent with embodiments of the disclosure.

In some embodiments of the present disclosure, the gratings shown in FIG. 2 can be replaced by the grating design shown in FIG. 3B, where the sub-grating blocks can also be joined as in FIG. 5.

Figure 4A:
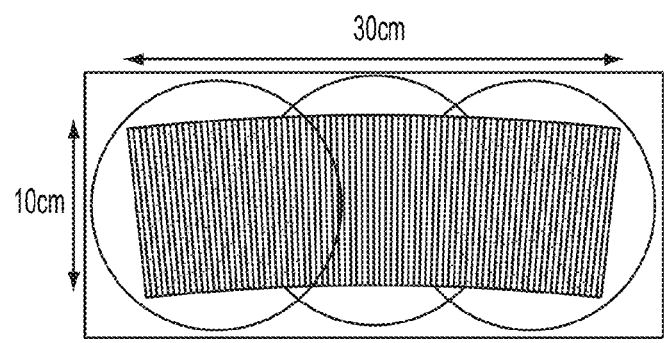
FIGS. 4A-4C shows an example design for a clinical scanner for large extremity joints consistent with embodiments of the disclosure, where
Figure 4B:
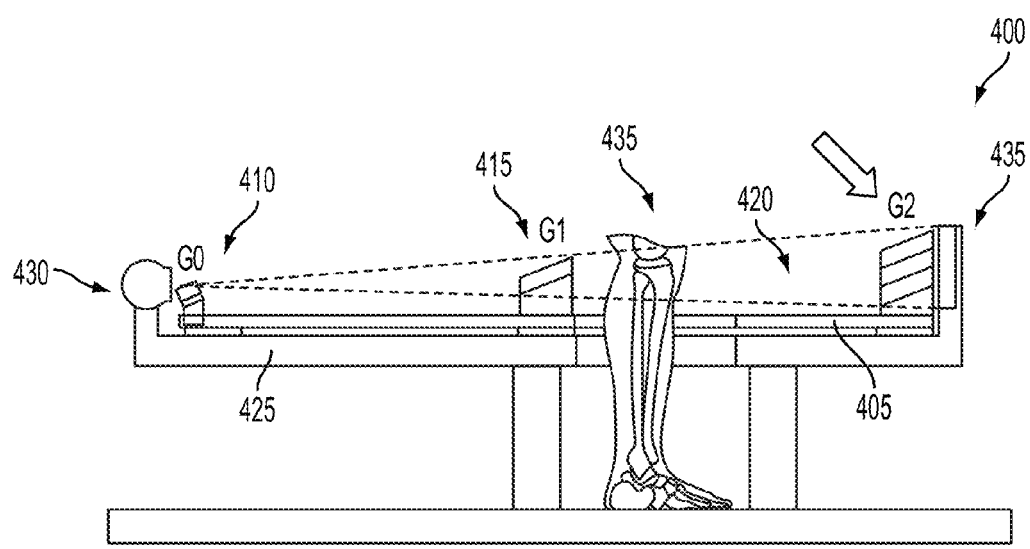
Figure 4C:
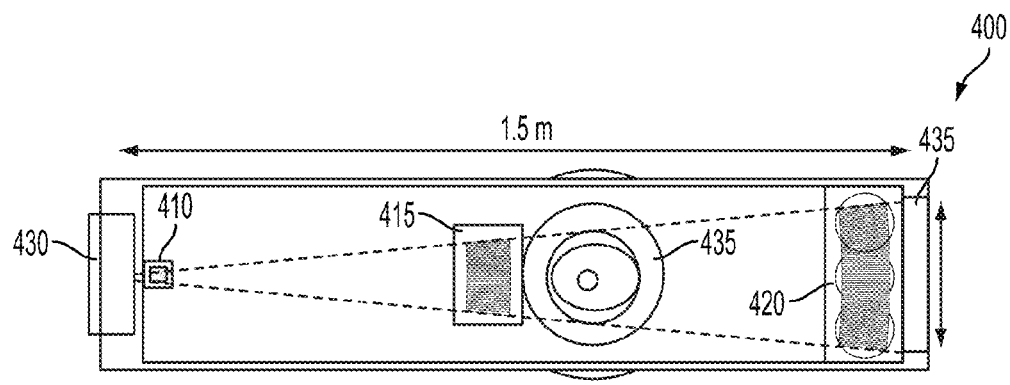

FIGS. 4A-4C show example views of a cone-beam GAI-CT scanner and imager that can be used for the clinical evaluation of extremity joints consistent with implementations of the present disclosure, where FIG. 4A shows a large FOV analyzer grating using three tiled wafers and FIGS. 4B and 4C show a side view and a top view of the scanner, respectively.

Figures 1A, 1B:
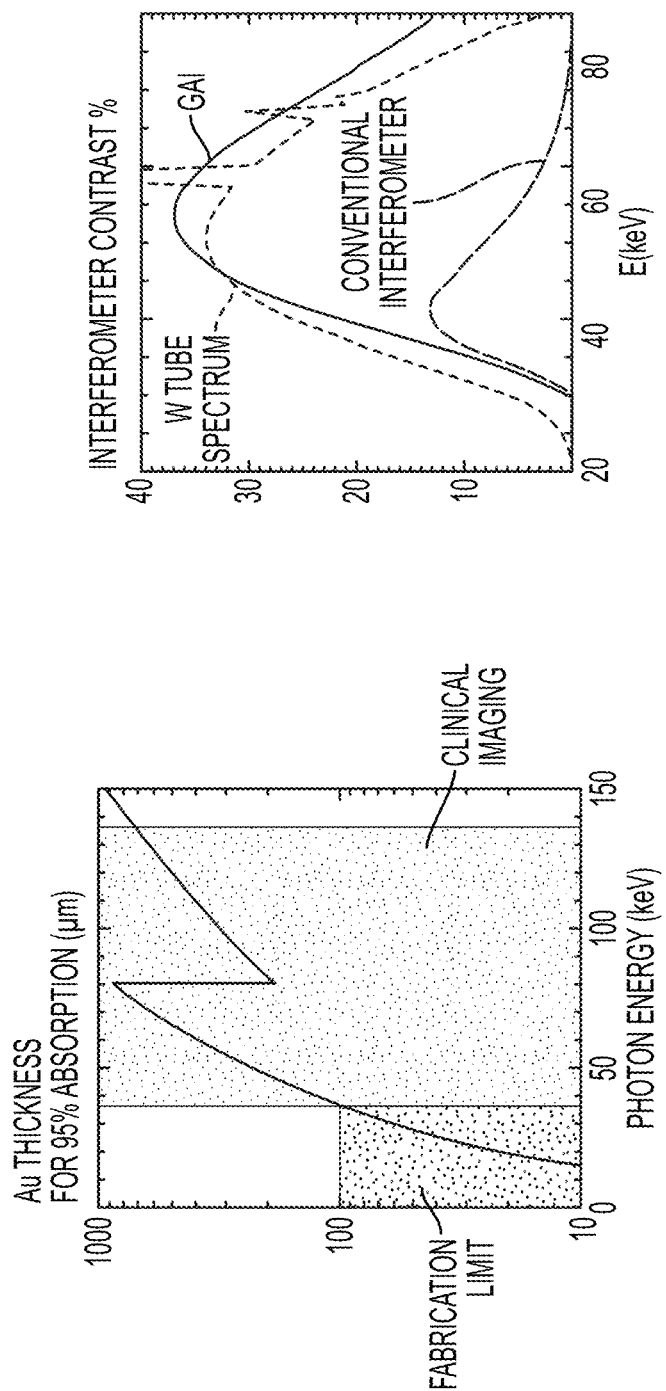
FIG. 1A shows gold thickness needed for 95% absorption, as a function of X-rays energy. Also shown in FIG. 1B the fringe contrast for a conventional grating interferometer having 100 μm thick, 4 μm period Au analyzer, and the contrast of a GAI interferometer having Au gratins of the same thickness, but inclined at 12°. In the conventional interferometer at energies of clinical interest the analyzer becomes transparent to X-rays, drastically reducing the interferometer contrast, while in the GAI case a much higher contrast of 30% is obtained. The spectrum of a W anode X-ray tube, after transmission through 2 mm Al and 150 mm soft tissue is also plotted in FIG. 1B.

The system can work between 75-100 kVp, corresponding to transmitted spectra with 55-65 keV mean energy for the average human knee. This range encompasses that optimal for attenuation CT of extremities (80-90 kVp). To maximize the angular sensitivity while having a clinically compatible system length, the system uses a symmetric GAI design with gratings of equal period of about 5 µm, 100-200 µm thickness, and operated in the $3^{rd}$ Talbot order (~1.5 m length), at ~12° glancing angle. Calculations have shown that the $3^{rd}$ order maximizes the product of the angular sensitivity and contrast and thus the DPC-CT SNR. The computed fringe contrast as a function of energy is shown in FIG. 1B, indicating high spectrally averaged contrast of ~30%.

The design of a large area tiled grating is shown in FIG. 4A. A 30 cm wide by 20 mm tall FOV is achieved by overlapping three 6" wafers, carrying each a 100×100 mm tiled grating array composed of 10 sub-gratings of 10 mm width, inclined at 12°. The sub-gratings are joined as shown in FIG. 5, which perturbs very little the grating pattern. For accurate positioning the wafers can be placed on a precision machined tray with clear apertures. The partial overlap between the grating substrates leads to only a small increase in beam attenuation. In some implementations, the tiled grating can have the fanned geometry, as shown in FIG. 3B. In some implementations, the tiled GAI gratings are used to achieve a wide (30 cm) FOV at the detector, while large FOV height is obtained by vertically stacking several rows of tiled GAIs. Alternately, 'slot-scan' DPC-CT systems can be built in which the object (e.g. a knee) is helically scanned with single row of GAI gratings.

FIGS. 4B and 4C show a side view and top view of the scanner 400, respectively. The scanner 400 includes a first arm 405 arranged to support the Talbot-Lau interferometer in a vibration free manner. The interferometer includes a source grating G0 410, a phase grating G1 415 and an analyzer grating G2 420. A second arm 425, separate from the first arm 405, is arranged to support the X-ray tube 430 and the detector 435. The first arm 405 and/or second arm 425 can be made of light, stiff, and thermally stable carbon honeycomb, such as used in space optics instrumentation as in known in the art. The scanner 400 can be mounted on a large bore stepper stage (not shown in detail) which will rotate it around a sample 435.

The X-ray tube 430 can be a dc tube instead of a pulsed one to eliminate the system or background phase variation due to pulsed X-ray heating of the source grating. An example of a suitable tube is the MXR-160HP/11 industrial tube made by Comet, Switzerland, delivering in dc mode up to ~25 mA at 80 kVp, and having dual spot capability (160 µm/400 µm in IEC336 standard). This X-ray tube provides a compact, light and vibration free X-ray source that is well suited for scanning together with the sensitive interferometer. Other similar type X-ray source could also be used as is known in the art.

The detector 435 can be a high efficiency, direct coupled CsI/CCD, such as the ARGUS model developed by Teledyne DALSA Inc. for panoramic imaging. This detector has about an order of magnitude higher sensitivity than a typical CMOS flat panel, and a wide form factor well suited for a slot-scan clinical system. The pixel size can be varied between 27-160 µm and the acquisition time is ≥0.125 s. Other similar type detectors could also be used as is known in the art.

Figure 6:
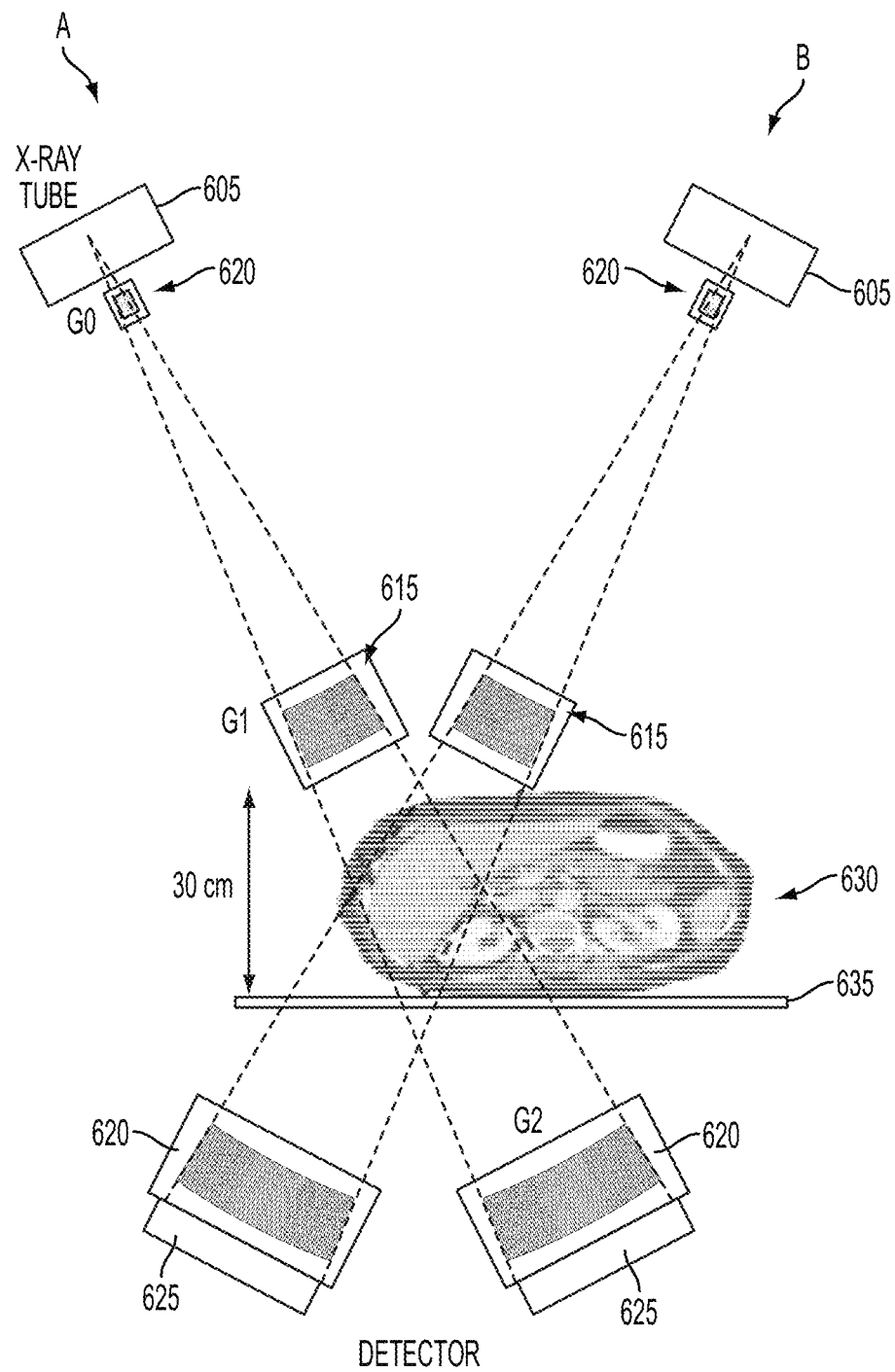
FIG. 6 shows an example top view of a GAI-TS (TS=tomosynthesis) scanner that can be used for the clinical evaluation of internal organs consistent with implementations of the present disclosure.

FIG. 6 shows an example top view of a GAI-TS scanner that can be used for the clinical evaluation of internal organs or tissues consistent with implementations of the present disclosure. The GAI-TS scanner can include x-ray source 605, i.e., x-ray tube, source grating G0 610, phase grating G1 615, analyzer grating G2 620, and detector 625. During scanning, object 630 is positioned between phase grating G1 615 and analyzer grating G2 620. The GAI-TS scanner constitutes a symmetric interferometer where source grating G0 610, phase grating G1 615, and analyzer grating G2 620 have equally spaced gratings of equal period. In this example, object 630, i.e., a person, is lying flat on a table 635 with x-ray source 605, source grating G0 610, phase grating G1 615 positioned above the person and analyzer grating G2 620 and detector 625 positioned below. As shown in FIG. 6, object 630 is about 25 cm in thickness; however, the thickness of object 630 is not critical to the arrangement of FIG. 6. Alternatively, object 630 can be positioned in a vertical position with x-ray source 605, source grating G0 610, phase grating G1 615 positioned on one side of the person and analyzer grating G2 620 and detector 625 positioned on the other. In one implementation, the GAI-TS scanner can have an overall length of about 1.7 m making the GAI-TS scanner suitable for a C-arm mount, as is known in the art.

In order to scan a wider area of object 630, x-ray source 605, source grating G0 610, phase grating G1 615, analyzer grating G2 620, and detector 625 can be arranged on a rotatable support structure (not shown). As shown in FIG. 6, the GAI-TS scanner can be rotated about object 630 between extreme positions A and B. Depending on the particular size of the GAI-TS and/or the size of object 630 being scanned, the GAI-TS can be rotated about object 630 through a variety of angular degrees, for example, ranging from about 45° to about 5°, or about 30° to about 10°. One of ordinary skill will appreciate that the implementations of the disclosure is not limited to the particular degree with which the GAI-TS can rotate. In particular, the limited angular scan can be used for the GAI-TS of internal organs, which allows viewing the organs while avoiding the thick bone in the spine which can decrease fringe contrast.

In implementations, source grating G0 410, source grating G0 610, phase grating G1 415, phase grating G1 615, analyzer grating G2 420, and analyzer grating G2 620 shown in FIGS. 4 and 6 are inclined at a glancing angle θ of about 15°. The glancing angle at which the gratings are inclined increases their effective thickness by a factor of about 4, which in turn increases by a factor between about 4 and 10 their X-ray absorption, enabling to obtain at high energy much higher contrast than possible with the conventional, normal incidence interferometer. Additionally, the grating can be 'tiled' a single substrate in a fanned geometry, as shown in FIG. 3B, to increase the horizontal FOV and to eliminate the lateral beam vignetting in the grating openings. To increase the vertical FOV, the gratings can be composed of more than one, i.e., three, gratings stacked on top of the other.

The grating arrangement of FIG. 3B can produce a high fringe contrast, which allows for a reduction in the exposure to the x-rays. X-ray exposure can be further reduced by combining the GAI with the 'interlaced phase-scanning' technique, which uses a single exposure per CT angle to retrieve the phase, and also enables a continuous scan as known in the art (Zanette et al. *Applied Physics Letters* 98, 094101 (2011). FIG. 7A shows an example of this method that comprises simultaneously scanning the position of one the gratings $x_g$ and the CT viewing angle ω, thus obtaining a phase image averaged over a small angular range (typically) ~1-2°. The combination of GAI with interlaced scanning enables DPC-CT at similar dose as in conventional CT. This is illustrated in FIG. 7B with the DPC-CT image of fresh pig soft tissues immersed in a 25 mm vial with water ('soft tissue phantom'), obtained at 45 keV mean energy with a 0.25° step interlaced scan of 200°, and a total dose of 8.3 mGy [Sarapata, A. and Stayman, J. W. and Finkenthal, M. and Siewerdsen, J. H. and Pfeiffer, F. and Stutman, D., Medical Physics, 41, 021904 (2014)]. This result also shows that the soft tissue contrast in DPC-CT remains superior to that in attenuation-CT (FIG. 7C), also at high energy and at low dose.

While, as shown above, it is possible to use GAIs to build DPC-CT scanners having wide enough FOV to cover an object the size of the knee, for joints inside the torso, such as the hip or shoulder, this approach would be too complex and costly. Much more practical would be to use a small FOV scanner (e.g., 3×3 inch at the object) and perform Region-of-Interest DPC-CT (ROI DPC-CT) of the joint under investigation. It was shown both theoretically and experimentally that DPC projections are better suited for ROI CT than conventional, attenuation based projections. In addition to enabling the use of smaller gratings, another benefit in ROI DPC-CT is that the effective does to the patient is much reduced.

Further on, limited-angle CT or tomosynthesis (TS) is another technique which enables high resolution and localized imaging of soft tissues with lower dose than full-scan CT. Another feature making DPC-CT attractive for medical applications is that it is predicted to have better properties with respect to Region-of-Interest reconstruction than attenuation-CT. This happens because the phase image is the derivative of the phase shift perpendicular to the CT direction, which makes it more compatible with CT algorithms with truncation handling ability, and allows imaging a small ROI inside a large object using only a limited FOV.

Figure 8A:
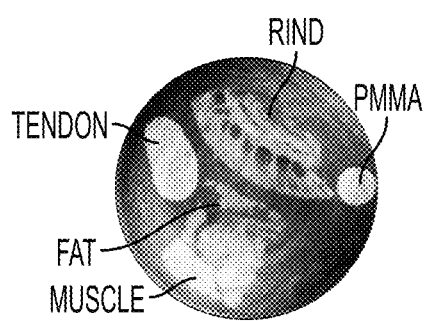
FIGS. 8A and 8B show a full-view and a ROI (ROI=Region-of-Interest) DPC-CT images of soft tissue phantom at 65 kVp, respectively.
Figure 8B:
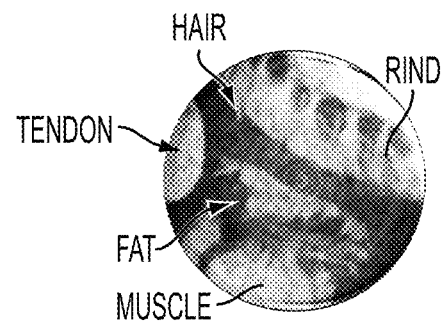

The theoretical, numerical and experimental investigations of ROI DPC-CT have shown that a small ROI can be accurately reconstructed in DPC-CT provided that a priori information on the electron density is known for a small region inside the ROI, e.g., a fluid or air cavity and can achieve considerably better contrast-to-noise ratio for the breast than attenuation-CT. As such, ROI DPC-CT is attractive for clinical applications at high X-ray energy. FIG. 8A shows a full-view DPC-CT image (FOV>100% of object extent) and FIG. 8B shows a ROI DPC-CT image (FOV~50% of object extent) of the soft tissue phantom at 65 kVp. As seen, there is essentially no loss of contrast or spatial resolution in the ROI image, with even small details such as a skin hair still apparent.

A further way of making clinical DPC practical is limited-angle CT or tomosynthesis. Limited-angle CT is particularly attractive for GAI-TS scanner configurations, discussed above, because it would allow imaging the internal organs without viewing the thick spine bone, which can decrease the interferometer contrast. The experimental DPC tomosynthesis studies at low energy are promising. For example, phase-contrast tomosynthesis images of a human finger can be obtained using a scan angle of only ~10° and using direct back-projection (BP) and filtered back-projection (FBP) DPC tomosynthesis algorithms, as is known in the art.

FIGS. 9A and 9B show images obtained by a simultaneous limited-angle and ROI DPC-CT using the GAI-TS scanner, as discussed above, at high energy. In particular, FIGS. 9A and 9B shows images of two slices of the pig soft tissue phantom, obtained at 65 kVp with full object coverage and full 200° CT scan (200°/100%) and with limited 50% object coverage and 50° limited-angle scan (50°/50%). FIG. 9C shows the attenuation images corresponding to those in 9B. As seen, the soft tissue contrast enhancement and resolution characteristic of full DPC-CT is maintained in the ROI/limited-angle CT images. Also encouraging is that this type of imaging works through bone, as illustrated in FIG. 9D which shows 200°/100% and 50°/50% CT images of the rind, obtained through several mm thick cortical bone.

Using a single image per CT angle as shown above, the clinical scanner, as shown in FIGS. 4B, 4C, and 6, will be able to perform a 400 step CT scan in ~50 s. A scan time of this order is also imposed by the photon flux available through the interferometer gratings. For instance, assuming 25 mA operation, 160 μm detector pixels, 1.5 m system length, 25% interferometer transmission, and the 80 kVp filtered spectrum in FIG. 1B, 30-40 photons will be recorded per pixel using 0.125 s integration, which is comparable to the typical photon count in a clinical CT system. For extremities, the above scan time is clinically acceptable, since the extremities can be easily immobilized for longer times. The scan time could be further shortened using a bright tube and faster detector.

To enable DPC-CT with clinically compatible dose, several dose reduction strategies can be implemented. The first is to use a single-image per angle scanning technique. In addition to the interlaced scanning above presented, there are two other methods: the Moire method, in which high frequency fringes are generated and spatial Fourier analysis used to obtain the attenuation, phase and scatter information, and the Reverse Projection, in which a 360° scan is used to sample two opposite points in the phase-scan curve.

Figure 10A:
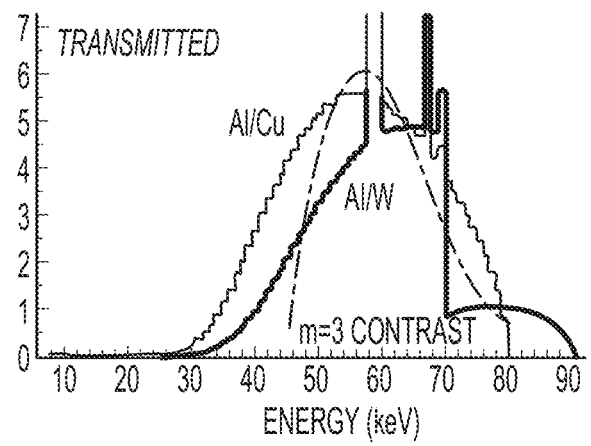
FIGS. 10A and 10B shows incident and transmitted spectra through 150 mm tissue, for 80 and 90 kVp W anode tube filtered with Al/Cu and with Al/W, respectively.
Figure 10B:
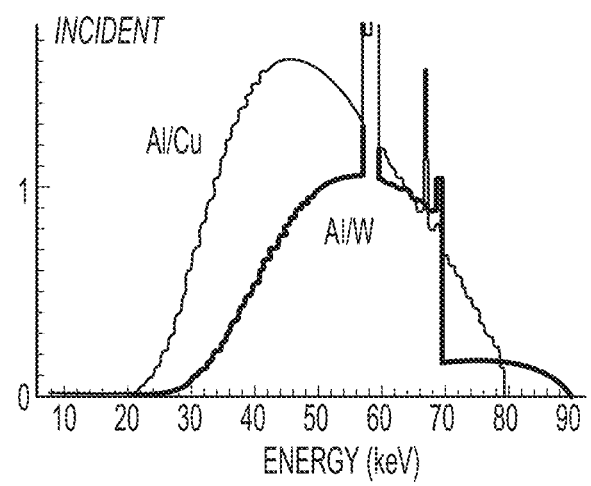

The second strategy is spectral filtering or shaping Spectral shaping is a much more powerful dose reduction tool in DPC-CT than in attenuation CT, because DPC uses for imaging strictly the transmitted radiation. Thus, it is possible to remove the low energy part of the X-ray spectrum which contributes most to the dose, without loss of phase contrast. This is illustrated in FIG. 10 which plots the contrast of a m=3 GAI of 60 keV mean energy, together with incident and transmitted W anode spectra through 150 mm of tissue. Two cases are compared: an 80 kVP spectrum filtered with 2 mm Al and 0.2 mm Cu, as used for attenuation-CT of extremities, and a 90 kVp spectrum filtered with 2 mm Al and 0.1 mm W. As seen, the W filtering cuts by ~200% the incident radiation outside the band of high contrast, while reducing by only about 25% the transmitted radiation in this band.

The dose to the knee computed with the PCXMC Monte-Carlo code is reduced from ~0.0012 mGy per mAs with the 80 kVp/Al/Cu spectrum, to ~0.0006 mGy per mAs with the 90 kVp/Al/W spectrum. It is thus possible to achieve ~80% dose reduction with only a modest scan time increase.

Finally, for dose reductions beyond those possible with hardware methods one can implement advanced reconstruction algorithms such as iterative reconstruction.

While the teachings has been described with reference to the exemplary embodiments thereof, those skilled in the art will be able to make various modifications to the described embodiments without departing from the true spirit and scope. The terms and descriptions used herein are set forth by way of illustration only and are not meant as limitations. In particular, although the method has been described by examples, the steps of the method may be performed in a different order than illustrated or simultaneously. Furthermore, to the extent that the terms "including", "includes", "having", "has", "with", or variants thereof are used in either the detailed description and the claims, such terms are intended to be inclusive in a manner similar to the term "comprising." As used herein, the term "one or more of" with respect to a listing of items such as, for example, A and B, means A alone, B alone, or A and B. Those skilled in the art will recognize that these and other variations are possible within the spirit and scope as defined in the following claims and their equivalents.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A differential phase contrast X-ray imaging system comprising:
    an X-ray illumination system;
    a beam splitter grating arranged in a radiation path of the X-ray illumination system and operable to receive an incident X-ray beam and provide an interference pattern of X-rays;
    a detector system arranged in a radiation path to detect X-rays after passing through the beam splitter grating and in a Talbot-Lau interferometer configuration with the beam splitter grating, wherein the detector system comprises a X-ray detector and an analyzer grating, wherein the analyzer grating comprises a plurality of sub-gratings arranged on a common substrate, the plurality of gratings including an edge sub-grating and a central sub-grating, wherein the edge sub-grating is tilted at an angle to the central sub-grating, wherein the analyzer grating is operable to intercept and block at least a portion of the interference pattern of X-rays before reaching the X-ray detector;
    a rotation stage operable to rotate the X-ray illumination system, the beam splitter grating, and the detection system about an object;
    wherein the beam splitter grating and the analyzer grating are arranged at a shallow angle relative to a plane characterized by a direction of the incident X-ray beam, wherein the shallow angle is less than 30° and wherein the detector is operable to capture a single image for each angle at which the rotation stage is rotated.

2. The differential phase contrast X-ray imaging system according to claim 1, wherein the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the longitudinal dimension and being spaced substantially parallel to each other in the lateral dimension such that there are optically rare regions between adjacent optically dense regions, wherein each optically dense region has a depth in the transverse dimension that is smaller than a length in the longitudinal dimension, wherein the analyzer grating is arranged with the longitudinal dimension at the shallow angle.

3. The differential phase contrast X-ray imaging system according to claim 1, wherein the beam splitter grating is a transmission grating.

4. The differential phase contrast X-ray imaging system according to claim 1, wherein the analyzer gratings comprises more than one grating tiled on top of each other.

5. The differential phase contrast X-ray imaging system according to claim 1, wherein the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the lateral dimension and being spaced in a divergent geometry from each other such that there are optically rare regions between adjacent optically dense regions, wherein each optically dense region has a depth in the transverse dimension that is smaller than a length in the longitudinal dimension and the lateral dimension, wherein the analyzer grating is arranged with the lateral dimension at the shallow angle.

6. The differential phase contrast X-ray imaging system according to claim 1, wherein the X-ray illumination system comprising:
    an X-ray source;
    a source grating arranged in a radiation path between the X-ray source and the beam splitter grating, wherein the source grating provides a plurality of substantially coherent X-ray beams.

7. The differential phase contrast X-ray imaging system according to claim 6, further comprising a vibration resistant mount operable to provide a support to the source grating, the beam-splitter grating, the analyzer grating.

8. The differential phase contrast X-ray imaging system according to claim 1, wherein the beam splitter grating and the analyzer grating have grating patterns determined according to Talbot-Lau conditions.

9. The differential phase contrast X-ray imaging system according to claim 1, wherein a field of view of the detector system is sized to image a human extremity.

10. A differential phase contrast X-ray imaging method comprising:
providing an incident X-ray beam using an X-ray illumination system;
receiving the incident X-Ray beam at a beam splitter grating that is arranged in a radiation path of the X-ray illumination system and providing an interference pattern of X-rays;
rotating a rotation stage that supports the X-ray illumination system, the beam splitter grating, and the detection system about an object;
detecting, using a detecting system arranged in a radiation path, X-rays after passing through the beam splitter grating that is in a Talbot-Lau interferometer configuration with the beam splitter grating, wherein the detector system comprises a X-ray detector and an analyzer grating, wherein the analyzer grating comprises a plurality of sub-gratings arranged on a common substrate, the plurality of gratings including an edge sub-grating and a central sub-grating, wherein the edge sub-grating is tilted at an angle to the central sub-grating, wherein the analyzer grating is operable to intercept and block at least a portion of the interference pattern of X-rays before reaching the X-ray detector; and
capturing a single image for each angle at which the rotation stage is rotated,
wherein the beam splitter grating and the analyzer grating are arranged at a shallow angle relative to a plane characterized by a direction of the incident X-ray beam, wherein the shallow angle is less than 30.

11. The differential phase contrast X-ray imaging method according to claim 10, wherein the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the longitudinal dimension and being spaced substantially parallel to each other in the lateral dimension such that there are optically rare regions between adjacent optically dense regions, wherein each optically dense region has a depth in the transverse dimension that is smaller than a length in the longitudinal dimension, wherein the analyzer grating is arranged with the longitudinal dimension at the shallow angle.

12. The differential phase contrast X-ray imaging method according to claim 10, wherein the analyzer grating comprises more than one grating tiled and stacked on top of each other.

13. The differential phase contrast X-ray imaging method according to claim 10, wherein the analyzer grating has a longitudinal dimension, a lateral dimension that is orthogonal to the longitudinal dimension and a transverse dimension that is orthogonal to the longitudinal dimension and the lateral dimension, the analyzer grating comprising a pattern of optically dense regions each having a longest dimension along the lateral dimension and being spaced in a divergent geometry from each other such that there are optically rare regions between adjacent optically dense regions, wherein each optically dense region has a depth in the transverse dimension that is smaller than a length in the longitudinal dimension and the lateral dimension, wherein the analyzer grating is arranged with the lateral dimension at the shallow angle.

14. The differential phase contrast X-ray imaging method according to claim 10, further comprising:
receiving the incident X-ray beam at a source grating that arranged in a radiation path between a X-ray source and the beam splitter grating; and
proving a plurality of substantially coherent X-ray beams to the beam splitter grating.

15. The differential phase contrast X-ray imaging method according to claim 10, further comprising determining grating patterns for the beam splitter grating and the analyzer grating according to Talbot-Lau conditions.

16. The differential phase contrast X-ray imaging method according to claim 10, wherein a field of view of the detector system is sized to image a human extremity.

* * * * *